US008778386B2

(12) United States Patent
Liu et al.

(10) Patent No.: US 8,778,386 B2
(45) Date of Patent: Jul. 15, 2014

(54) ANTI-MICROBIAL SUBSTRATES WITH PEROXIDE TREATMENT

(75) Inventors: Kou-Chang Liu, Appleton, WI (US); David W. Koenig, Menasha, WI (US); Ali Yahiaoui, Roswell, GA (US); Alison Salyer Bagwell, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1455 days.

(21) Appl. No.: 11/847,976

(22) Filed: Aug. 30, 2007

(65) Prior Publication Data

US 2008/0138373 A1  Jun. 12, 2008

Related U.S. Application Data

(63) Continuation-in-part of application No. 11/301,546, filed on Dec. 13, 2005, now abandoned.

(51) Int. Cl.
  *A61F 13/00* (2006.01)
  *A61K 33/40* (2006.01)

(52) U.S. Cl.
  CPC ..................................... *A61K 33/40* (2013.01)
  USPC ........................................................ 424/443

(58) Field of Classification Search
  None
  See application file for complete search history.

(56) References Cited

U.S. PATENT DOCUMENTS

| 3,376,110 A | 4/1968 | Shiraeff |
| 3,480,557 A | 11/1969 | Shiraeff |
| 3,585,104 A | 6/1971 | Kleinert |
| 3,649,194 A | 3/1972 | Glanville |
| 3,755,185 A | 8/1973 | Waldmann et al. |
| 3,903,244 A | 9/1975 | Winkley |
| 4,059,678 A | 11/1977 | Winkley |
| 4,100,324 A | 7/1978 | Anderson et al. |
| 4,259,383 A * | 3/1981 | Eggensperger et al. ........ 428/72 |
| 4,375,448 A | 3/1983 | Appel et al. |
| 4,494,278 A | 1/1985 | Kroyer et al. |
| 4,514,345 A | 4/1985 | Johnson et al. |
| 4,528,239 A | 7/1985 | Trokhan |
| 4,594,130 A | 6/1986 | Chang et al. |
| 4,640,810 A | 2/1987 | Laursen et al. |
| 4,654,208 A | 3/1987 | Stockel et al. |
| 4,781,974 A | 11/1988 | Bouchette et al. |

(Continued)

FOREIGN PATENT DOCUMENTS

| EP | 0002594 B1 | 12/1982 |
| EP | 0173450 A2 | 3/1986 |

(Continued)

OTHER PUBLICATIONS

English language abstract of Japanese Patent No. 10101310 published Apr. 21, 1998.

(Continued)

*Primary Examiner* — Brian Gulledge
(74) *Attorney, Agent, or Firm* — Dority & Manning, P.A.

(57) ABSTRACT

An oxidizing anti-microbial treatment and products containing such treatment are described. The treatment involves, in part, preparing a substrate to accept an attachment of charged moieties, and a number of stabilized peroxide compounds on at least part of a surface of said substrate. When microbes, such as bacteria, having a net charge opposite to that of the charged moieties come in close proximity to the treated substrate surface, peroxide molecules from the substrate are activated and released to kill the microbes.

19 Claims, 3 Drawing Sheets

(56) References Cited

U.S. PATENT DOCUMENTS

| | | |
|---|---|---|
| 4,793,898 A | 12/1988 | Laamanen et al. |
| 4,802,473 A | 2/1989 | Hubbard et al. |
| 4,818,464 A | 4/1989 | Lau |
| 4,835,019 A | 5/1989 | White et al. |
| 4,847,089 A | 7/1989 | Kramer et al. |
| 4,853,978 A | 8/1989 | Stockum |
| 4,969,457 A | 11/1990 | Hubbard et al. |
| 5,008,093 A | 4/1991 | Merianos |
| 5,020,533 A | 6/1991 | Hubbard et al. |
| 5,031,245 A | 7/1991 | Milner |
| 5,098,522 A | 3/1992 | Smurkoski et al. |
| 5,133,090 A | 7/1992 | Modak et al. |
| 5,180,605 A | 1/1993 | Milner |
| 5,183,901 A | 2/1993 | Login et al. |
| 5,260,171 A | 11/1993 | Smurkoski et al. |
| 5,261,421 A | 11/1993 | Milner |
| 5,275,700 A | 1/1994 | Trokhan |
| 5,322,061 A | 6/1994 | Brunson |
| 5,328,565 A | 7/1994 | Rasch et al. |
| 5,334,289 A | 8/1994 | Trokhan et al. |
| 5,383,450 A | 1/1995 | Hubbard et al. |
| 5,389,202 A | 2/1995 | Everhart et al. |
| 5,431,786 A | 7/1995 | Rasch et al. |
| 5,487,896 A | 1/1996 | Modak et al. |
| 5,496,624 A | 3/1996 | Stelljes, Jr. et al. |
| 5,500,277 A | 3/1996 | Trokhan et al. |
| 5,514,523 A | 5/1996 | Trokhan et al. |
| 5,527,171 A | 6/1996 | Soerensen |
| 5,553,608 A | 9/1996 | Reese et al. |
| 5,554,467 A | 9/1996 | Trokhan et al. |
| 5,566,724 A | 10/1996 | Trokhan et al. |
| 5,595,628 A | 1/1997 | Gordon et al. |
| 5,620,527 A | 4/1997 | Kramer et al. |
| 5,624,790 A | 4/1997 | Trokhan et al. |
| 5,628,876 A | 5/1997 | Ayers et al. |
| 5,725,867 A | 3/1998 | Mixon |
| 5,813,398 A | 9/1998 | Baird et al. |
| 5,906,823 A | 5/1999 | Mixon |
| 5,993,839 A | 11/1999 | Mixon |
| 6,136,775 A * | 10/2000 | Strout et al. ............ 510/439 |
| 6,387,379 B1 | 5/2002 | Goldberg et al. |
| 6,432,270 B1 | 8/2002 | Liu et al. |
| 6,511,580 B1 | 1/2003 | Liu |
| 6,576,087 B1 | 6/2003 | Liu |
| 6,582,558 B1 | 6/2003 | Liu |
| 6,727,004 B2 | 4/2004 | Goulet et al. |
| 6,805,965 B2 | 10/2004 | Liu |
| 6,887,350 B2 | 5/2005 | Garnier et al. |
| 2002/0142690 A1* | 10/2002 | Wilson ...................... 442/400 |
| 2003/0235605 A1 | 12/2003 | Lelah et al. |
| 2004/0009141 A1* | 1/2004 | Koenig et al. ........... 424/70.28 |
| 2004/0009210 A1 | 1/2004 | Koenig et al. |
| 2004/0151919 A1 | 8/2004 | Bagwell et al. |
| 2005/0137540 A1 | 6/2005 | Villanueva et al. |
| 2006/0051384 A1* | 3/2006 | Scholz et al. ............ 424/405 |
| 2007/0134302 A1 | 6/2007 | Koenig et al. |
| 2008/0033091 A1* | 2/2008 | Bohrer et al. ............ 524/438 |

FOREIGN PATENT DOCUMENTS

| | | | |
|---|---|---|---|
| EP | 0256369 A2 | 2/1988 | |
| EP | 0288419 A1 | 10/1988 | |
| EP | 0346835 A2 | 12/1989 | |
| EP | 0429224 A1 | 5/1991 | |
| EP | 0447582 A1 | 9/1991 | |
| EP | 0463202 A1 | 1/1992 | |
| EP | 0284132 B1 | 1/1994 | |
| EP | 0300814 B1 | 11/1994 | |
| EP | 0467869 B1 | 3/1995 | |
| EP | 0456627 B1 | 6/1995 | |
| EP | 0350147 B1 | 7/1995 | |
| EP | 0831056 A2 | 3/1998 | |
| EP | 0700428 B1 | 8/1998 | |
| EP | 0728181 B1 | 3/1999 | |
| EP | 1034801 A1 | 9/2000 | |
| EP | 1133982 A2 | 9/2001 | |
| JP | 11-313790 A | 11/1999 | |
| WO | WO 9531102 | 11/1995 | |
| WO | WO 9810737 | 3/1998 | |
| WO | WO 9821220 | 5/1998 | |
| WO | WO 9821305 | 5/1998 | |
| WO | WO 9952362 | 10/1999 | |
| WO | WO 2006/040067 * | 4/2006 | ............ C08K 3/18 |

OTHER PUBLICATIONS

English language abstract of Japanese Patent No. 11323634 published Nov. 26, 1999.

"A Guide to Freeze drying for the Laboratory." LABCONCO, Kansas City, MO. 2004: 12 pages <www.labconco.com>.

Habash M. et al. "Microbial Biofilms: Their Development and Significance for Medical Device-Related Infections," Journal of Clinical Pharmacology, vol. 39, p. 887-898: 1999.

International Search Report, PCT/IB2008/052512, dated Jun. 24, 2008.

* cited by examiner

ANTI-MICROBIAL SUBSTRATES WITH PEROXIDE TREATMENT

RELATED APPLICATIONS

The present application is a continuation-in-part application and claims priority to U.S. patent application Ser. No. 11/301,546 filed on Dec. 13, 2005 now abandoned.

BACKGROUND

In recent years, the prevalence of nosocomial infections has had serious implications for both patients and healthcare workers. Nosocomial infections are those that originate or occur in a hospital or long-term care, hospital-like settings. In general nosocomial infections are more serious and dangerous than external, community-acquired infections because the pathogens in hospitals are more virulent and resistant to typical antibiotics. Nosocomial infections are responsible for about 20,000-100,000 deaths in the United States per year. About 5% to 10% of American hospital patients (about 2 million per year) develop a clinically significant nosocomial infection. These hospital-acquired infections (HAIs) are usually related to a procedure or treatment used to diagnose or treat the patient's illness or injury.

The mechanism of action of nosocomial infections, as in any other infectious disease, is dependent on host, agent and environment factors. Risk factors for the host are age, nutritional status and co-existing disorders. Nosocomial infections are influenced by the microbes' intrinsic virulence as well as its ability to colonize and survive within institutions. Diagnostic procedures, medical devices, medical and surgical treatment are risk factors in the hospital environment. Hospital-acquired infections can be caused by bacteria, viruses, fungi, or parasites. These microorganisms may already be present in the patient's body or may come from the environment, contaminated hospital equipment, healthcare workers, or other patients. Depending on the causal agents involved, an infection may start in any part of the body. A localized infection is limited to a specific part of the body and has local symptoms.

In today's healthcare environment, the battle against nosocomial infections has not yet been won. Even though hospital infection control programs and a more conscientious effort on the part of healthcare workers to take proper precautions when caring for patients can prevent about 25% to 33% of these infections, a significant number of infections still occur. The current procedures are not sufficient. Despite enforcement of precautionary measures (e.g. washing hands, wearing gloves, face mask and cover gowns), HAIs still occur predominately via contact transfer. That is, individuals who contact pathogen-contaminated surface such as hands, clothing and/or medical instruments, can still transfer the pathogens from one surface to another immediately or within a short time after initial contact. Researchers have employed numerous ways to attack microbe related issues. Antiseptics and disinfectants are used extensively in hospitals and other health care settings for a variety of topical and hard-surface applications. In particular, they are an essential part of infection control practices and aid in the prevention of nosocomial infections. Conventional anti-microbial agents currently available, however, are not very effective at killing and immobilizing pathogens on to the surfaces to which the anti-microbial agents are applied.

The problem of anti-microbial resistance to biocides has made control of unwanted bacteria and fungi complex. The widespread use of antiseptic and disinfectant products has prompted concerns about the development of microbial resistance, in particular cross-resistance to antibiotics. A wide variety of active chemical agents (or "biocides") are found in these products, many of which have been used for hundreds of years for antisepsis, disinfection, and preservation. Despite this, less is known about the mode of action of these active agents than about antibiotics. In general, biocides have a broader spectrum of activity than antibiotics, and, while antibiotics tend to have specific intracellular targets, biocides may have multiple targets. The widespread use of antiseptic and disinfectant products has prompted some speculation on the development of microbial resistance, in particular cross-resistance to antibiotics. This review considers what is known about the mode of action of, and mechanisms of microbial resistance to, antiseptics and disinfectants and attempts, wherever possible, to relate current knowledge to the clinical environment.

Antibiotics should only be used when necessary. Use of antibiotics creates favorable conditions for infection with the fungal organism *Candida*. Overuse of antibiotics is also responsible for the development of bacteria that are resistant to antibiotics. Furthermore, overuse and leaching of anti-microbial agents or antibiotics can cause bioaccumulation in living organisms and may also be cytotoxic to mammalian cells.

To better protect both patients and healthcare providers, protective articles, such as garments, gloves, and other coverings that have fast-acting, highly efficient, anti-microbial properties, including antiviral properties, are need for a variety of different applications for wide spectrum anti-microbial protection. The industry needs anti-microbial materials that can control or prevent contact transfer of pathogens from area to area and from patient to patient. In view of the resistance problems that may arise with conventional anti-microbial agents that kill when bacteria ingest antibiotics, an anti-microbial that kills virtually on contact and has minimal or no harmful byproducts or residue afterward would be well appreciated by workers in the field. Hence, it is important to develop materials that do not provide a medium for the pathogens to even intermittently survive or grow upon, and that are stably associated to the substrate surfaces on which the anti-microbial agent is applied. Moreover, the anti-microbial protective articles should be relatively inexpensive to manufacture.

In addition, a need exists for an anti-microbial material that also can be applied to consumer products, such as facial tissues, bath tissues, paper towels, wet wipes and the like. In particular, a need exists for an anti-microbial material than can be applied to any of the above products without causing any significant irritation to the user.

SUMMARY

The present invention pertains to a protective or cleaning article that has an exterior surface with at least a partial coating or layer of a stabilized peroxide compound associated with the exterior surface, which can be used for anti-microbial uses. The protective or cleaning article can be made from a variety of polymer-based materials and/or cellulosic materials, depending on the particular configuration and use of the article. For instance, the article can have a substrate that is composed in part from a natural or synthetic polymer latex film, natural cellulose fibers or weave, or a flexible non-woven web (e.g., spunbond, meltblown, or laminate combinations thereof (e.g., SMS)). Both the latex film and non-woven web can be elastomeric. The non-woven web can have either machine-direction (MD) or cross-directionally (CD)

elastic characteristics. In the realm of medical or infection-control uses, for example, latex films are typically part of protective articles such as gloves, and non-woven webs are used in face masks and cover gown. In household or cleaning applications, elastomeric latex films and non-woven materials can be fashioned into a number of products. For instance, cleaning wipes take up and trap dirt, or gloves protect a user's hands from contacting or transferring the dirt. The presence of a peroxide releasing compound on the surface of such article can greatly enhance their cleaning and anti-microbial benefits.

Other features and aspects of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
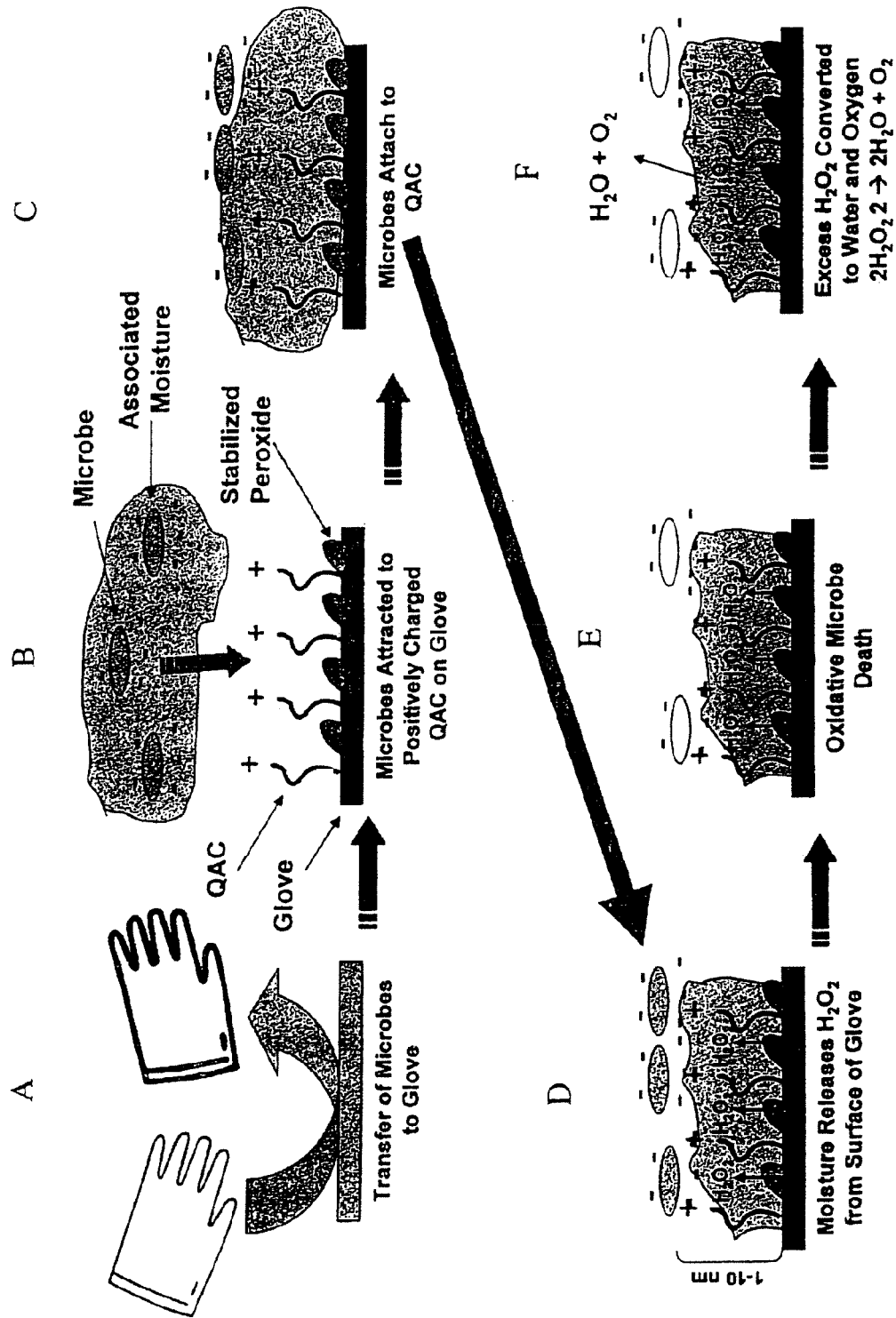
FIG. 1 is a series of schematic diagrams illustrating the anti-microbial mechanism of the present invention.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

Section A

The anti-microbial efficacy and potency of biocides are highly dependent on several chemical, physical, and environmental factors. Among these factors, the more important ones include the formulation and concentration of active agents, temperature, pH, duration of exposure, the physiological state and population size of the target microbes, and the presence of ions and organic matter. Also, the physical and chemical characteristics of the substrate to be disinfected can be important because of the interaction that the substrate may have with the biocide.

The inactivation or killing of microorganisms by means of either controlling their reproductive or metabolic activities typically is not an instantaneous event. In most situations, the greater the concentration of a particular anti-microbial agent, the faster the rate of microorganism inactivity, or the longer duration of exposure of a microbe to a disinfectant or biocide, the greater the anti-microbial effectiveness increases.

In recent years, a fast-acting anti-microbial treatment that is non-leaching from products or substrate surfaces has been in demand. The active agent of the anti-microbial treatment should not be either harmful to human skin or result in a toxic residue, which may breed resistant microbial strains. The active agents of the anti-microbial composition, if released into the immediate microenvironment decompose into benign components, predominantly oxygen and water, which are non-toxic to human skin or mammalian physiological systems.

At present, biocides can be categorized into four classes. They include: 1) toxic organic chemicals, 2) surfactant-based compounds, 3) metal or metallic molecules, and 4) oxidizing anti-microbial agents. Toxic organic chemicals that include, for example, thiazoles, thiocynates, isothiazolins, cyanobutane, dithiacarbamates, thione, triclosans, and bromo-compounds, while effective, have a residual toxicity in the local environment than can be harmful to the human user. Likewise, metal compounds are usually slow acting, environmentally persistent and toxic. Surfactants can be disrupt bacterial cell membranes, but they are also relatively-slow acting, not always broad spectrum, and persistent. On the other hand, oxidizing compounds have a broad spectrum and kill microbes rapidly. A shortcoming of conventional oxidizing preparations is that they are relatively short duration. The oxidizing anti-microbial agents include such compounds as halogens, halogen-containing polymers, chlorine dioxide, hydrogen peroxide, and ozone, which are relatively fast-acting and having a broad biocide spectrum.

The present invention describes a substrate that has a charged surface to readily attract oppositely charged microbes, such as bacteria, fungi and viruses, and at least a partial coating or layer of a stabilized peroxide compound. For examples, cationic molecules will attract and bind negatively charged microbes. Also disposed on the substrate surface is a plurality of stabilized oxidizing compounds. When activated in the presence of free moisture, such as liquid water or water vapor, the oxidizing compound releases from the surface. As one of the best kinds of biocides, oxidizing compounds provide effective quick-kill and broad-spectrum action, with minimal potential to develop antibacterial resistance. Oxidizing compounds such as hydrogen peroxides have been used for cleaning wounds or surgical sites after closure. The activity of peroxides is greatest against anaerobic bacteria. Furthermore, hydrogen peroxide has virucidal properties.

The present invention provides a simple and elegant mechanism for addressing the build up of often toxic agents on treated surfaces. FIG. 1 depicts in a series of schematic diagrams one way the present invention kills adsorbed microbes. In the embodiment, FIG. 1A shows a glove coming in contact with a contaminated surface or skin, and transferring the microbial contaminants to the surface of the glove. FIG. 1B is a magnified view at the surface of the glove as microbes come into contact with the glove substrate. Microbes typically exist in environments that allow for a micro-envelope of moisture surrounding their cells. According to the embodiment shown, negatively charged microbes are attracted to cationic moieties on the surface of the glove. In other embodiments, negatively charged surface moieties can be adapted to draw in positively charged microbes. A number of stabilized peroxide molecules are situated on the surface of the glove substrate. When the microbes attach to the cationic moieties, the micro-envelope of moisture around the microbes also draws near and interacts with the glove surface, activating and releasing peroxide from the surface, as illustrated in FIGS. 1C and 1D. The oxidative effect of the peroxide release kills the microbes that have become attached to the substrate in FIG. 1E. Excess hydrogen peroxide generated by the system, instead of becoming a problem, will decompose to harmless water and molecular oxygen and dissipates from the microenvironment of the substrate as illustrated in FIG. 1F.

Figure 2:
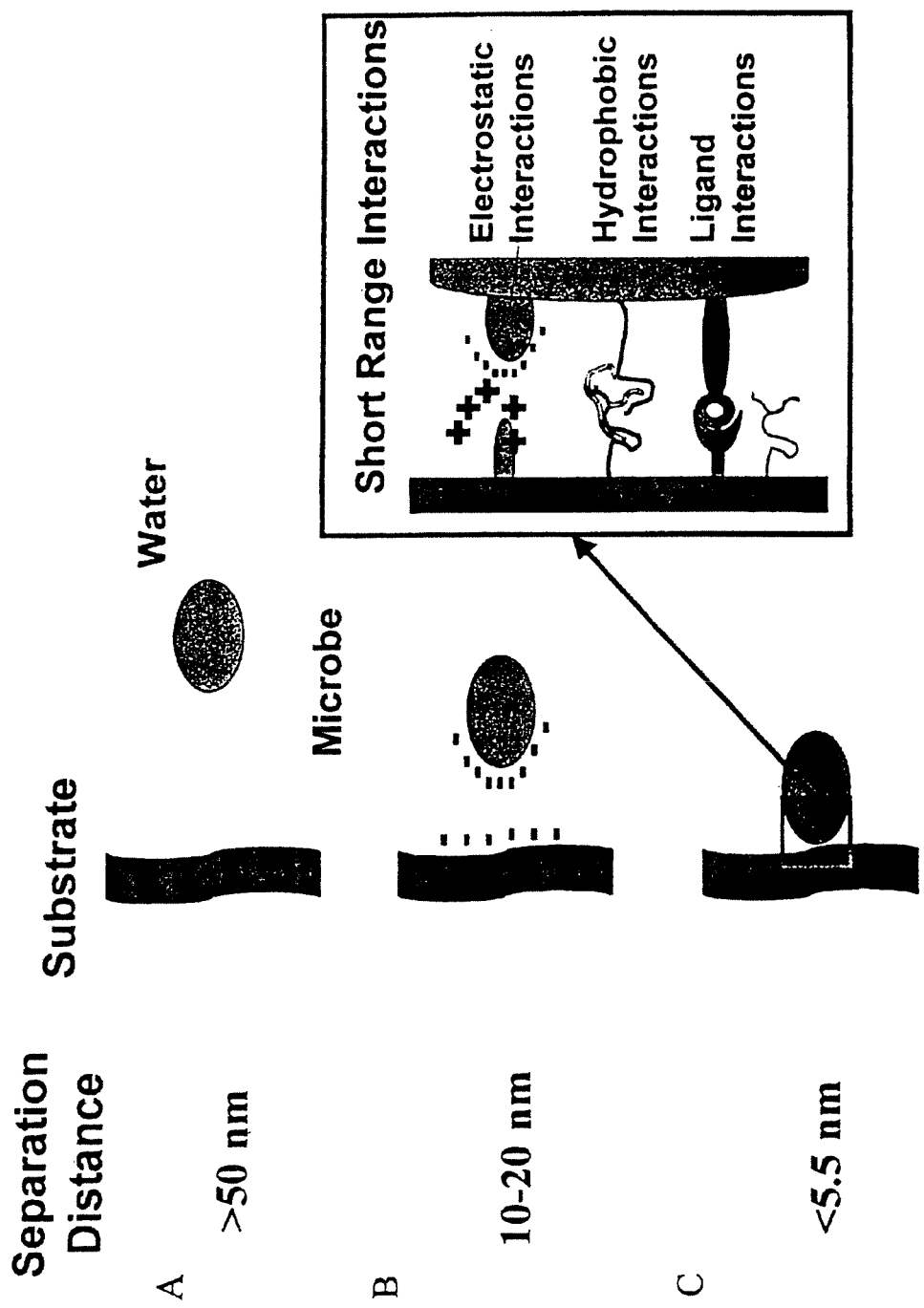
FIG. 2 is a series of schematic representations illustrating the interaction between a microbe and a substrate surface.

FIG. 2 shows a series of schematic panels illustrating the interaction of a microbe with a substrate surface. The microbe can be present either in a liquid medium, such as water, or have a moisture or biological envelope around its outer surface or cellular membrane. The diagram shows the relative distances between the microbe and the substrate surface and the different physical or chemical events as the microbe approaches the substrate. In the top panel, the microbe is greater than 50 nm away from the substrate; there is minimal interaction between the two. As the microbe approaches to within about 25 nm, electrostatic charge interactions between the substrate and microbe begin to appear. At relatively close distances of less than about 10 nm or 5 nm from the substrate, three kinds of significant surface to microbe interactions either strength or begin to occur. These typically involve: electrostatic, hydrophobic, or ligand interactions. (See, Habash, M. and G. Reid, Microbial Biofilms: Their Development and Significance for Medical Device-Related Infections, J. Clinical Pharmacology 39:887-898, 1999.) When in close proximity to the surface, the effective peroxide-release atmosphere about the coated substrate surface is within about 100 nm of the surface, more typically within 50 nm. Desirably, the peroxide micro-atmosphere is operational within about 20-25 nm, and optimal within about 5-10 nm of the surface.

Most biological entities have a net negative charge, positively charged membrane organisms will want to go to the membrane, targeted concentration. Charges moieties such as cationic compounds impart a charge to the substrate surface to attract charged microbes into close proximity with the peroxide prepared substrate surface. The cationic compounds contained in the products of the present invention appear to electrostatically interact with contaminants and other soils and inorganic particles, which contact the surface of the protective article and binds the contaminant such that it may be secured away from a user's skin. As used herein, the term "contaminant" should be read to include Gram negative and Gram positive bacteria, fungi and fungal spores, yeasts, molds and mold spores, protozoan, and viruses.

Hydrogen peroxide is a broad spectrum oxidizing agent, and is often used to clean wounds. When peroxide is released in sufficient quantities in a microenvironment, such as against potentially harmful organic compound molecules or microorganisms, peroxide will oxidize the compounds and/or surface lipids, proteins, or carbohydrates. Typically, since cellular membranes or viral caspids contain at least one of these three components, extreme oxidization will overwhelm the natural ability of microorganisms to cope with oxidation, and either denature the cellular membrane, rendering cellular metabolic reactions inoperative, or rupture the virus, releasing its genetic material and killing the organism. The resulting molecular oxygen and water vapor are benign by products that overcome the problem of persisting toxins in the environment. The activity of peroxides is greatest against anaerobic bacteria.

Stabilized peroxides have been blended in solutions with iodophores or quaternary ammonium compound, which have been used for disinfection of equipment surfaces. Stabilized peroxides are effective against a broad range of pathogens, such as both enveloped and non-enveloped viruses, vegetative bacteria, fungi, and bacterial spores. Similar to formulations found in peroxide-containing tooth gel or paste, the peroxide containing salts or compounds can be mixed with stabilizers that prevent the peroxide from releasing prematurely. It is desired that only in the presence of a sufficient amount of moisture will the peroxide react.

The hydrogen peroxide sources can be selected from a group including perborate compounds, percarbonate compounds, perphosphate compounds, and/or mixtures thereof. According to an embodiment, the stabilized peroxide-containing compound can be in the form of a carbohydrate mixture or salt. For example, as described in detail in U.S. Pat. No. 6,887,496, the contents of which are incorporated herein, the oxygen producing compounds for incorporation may include, for example, a carbohydrate-hydrogen peroxide mixture which has been crystallized into a stable crystalline material. Preferably, the oxygen producing compound is a crystalline compound comprised of a sugar alcohol-hydrogen peroxide mixture, such as mannitol-hydrogen peroxide or sorbitol-hydrogen peroxide. Polysaccharides such as cyclodextrin serve as carriers for organic peroxides. Guest-host complexes in which the cyclodextrin hosts stability holds the guest peroxide molecule or compounds; in particular, organic type of peroxides typically have a hydrophobic moiety that is situated in the cavity of the host while the peroxide moiety extend outside to react with the microbes.

The attractive forces, such as electrostatic, hydrogen bonding, polar, apolar, or van der waals forces, between the peroxide and the carrier molecules can be tailored to control the kinetics of peroxide release or interaction with the environment. Alternatively one can design the carrier to regulate the extent or level of exposure that the peroxide moieties have with the outside environment. A carrier, such as cyclodextrin, can encapsulate in-part or fully the peroxide moieties. Alternatively, one can use ligand or chelation mechanisms to regulate the exposure of the peroxide moiety to environmental hydrogen or organic molecules that may trigger the release of active peroxide.

Water soluble polymers can be employed as carrier for the peroxide salts. Some other materials that can be used to make the peroxide compound may be applied as a salt, and may include, for example, urea peroxide or urea hydrogen peroxide ($CH_4N_2O.7H_2O_2$) (Also referred to as carbamide peroxide. See, "Regulatory and Ingredient Use Information," regarding the labeling names for U.S. OTC Drug Ingredients in Volume 1, Introduction, Part A.), employed in stabilized amides (including salts; excluding alkanolamides and alkoxylated amides); sodium carbonate peroxide ($CH_2O_3$. $3/2H_2O_2.2Na$) (peroxy-sodium carbonate or sodium percarbonate); calcium peroxide ($CaO_2$) oxidizing agent; PVP-hydrogen peroxide, a complex of polyvinylpyrrolidone and hydrogen peroxide (($C_6H_9NO)_x.1/2H_2O_2$); or 2-pyrrolidinone, 1-ethenyl-, homopolymer, compounded with hydrogen peroxide ($H_2O_2$) (2:1). Ethylhydroxyethyl cellulose can be a carrier for hydrogen peroxide or other peroxides.

It is envisioned that certain stabilizer components can be incorporated to prevent a mass activation and release of peroxide when the coated substrate is exposed to an aqueous environment or other liquids. For instance, a stabilizer or carrier molecule can be covalently attached to the substrate by means of radiation grafting and load the peroxide moieties onto the covalently attached carriers. A radiation-induced graft polymerization of a hydrophilic monomer onto a substrate can take the form of a hydrogel graft, according to a method such as described in U.S. Pat. No. 6,387,379, incorporated herein, which can act as a host for a peroxide compound, thus forming a hydrogel-peroxide complex. A hydrogel is a hydrophilic polymer that can be crosslinked to form a cohesive network so that it swells in water but does not necessarily readily dissolve in water. For instance, a hydrophilic monomer such as N-vinyl pyrrolidone (NVP) can be used. Other hydrophilic monomers listed in U.S. Pat. No. 6,387,379 can also be used. As for radiation sources, ultraviolet (UV), gamma ray, or electron beam can be used.

An example of a formulation (Table 1) would contain a mixture of quaternary ammonium compounds (QACs) and stabilized peroxide, such as urea peroxide, calcium peroxide, sodium carbonate peroxide, mannitol and/or sorbitol peroxide. Urea peroxide, also known as carbamide peroxide, is a common ingredient in tooth paste and other dental bleeching systems. A formulation containing about 10% carbamide peroxide exhibits a similar level of active agent as another formulation containing about 3.3% hydrogen peroxide. The amount of stabilized peroxide present on the treated substrate can be up to about 20 percent by weight, but more typically is present at about 10-12 or 15 percent by weight in certain applications. Desirably, the amount of active peroxide on the surface can be about up to about 7 or 8 percent, such as about up to about 4 or 5 percent. Still, in other embodiments, only a small amount of active peroxide may be needed in order for the composition to provide sufficient anti-microbial activity. For instance, the amount of active peroxide on the surface can be less than about 2 percent, such as from about 0.1 percent to about 2 percent.

TABLE 1

Formulation

| Ingredient (Wt. %) | Formula 1 | Formula 2 |
| --- | --- | --- |
| Stabilized peroxide | 1-20% | 1-15% |
| Quanternary Ammonium Compound (QAC) | 4.0% | 2% |
| Cetyl pyrridinium chloride | 0.1% | 0.1% |
| Q25211 wetting agent | 0.01% | 0.01% |
| Anti-foaming agent | 0.002% | 0.002% |
| Deionized water | QS | QS |

A complex carbohydrate-hydrogen peroxide mixture, according to an embodiment, is introduced into or onto a substrate in an amount sufficient to produce a stream of oxygen upon insult such that it hinders the metabolism of microbes on and near the surface of the treated substrate. The mixture is capable of generating oxygen upon activation, and the oxygen acts as a terminal electron acceptor for bacteria on or near the substrate surface, such that the bacteria is either killed or the production of toxic or volatile organic compounds by bacterial is reduced or neutralized.

A fast-acting oxidizing microenvironment is neutral or benign to humans, mammals, or other macroorganism, but can be deadly to most microorganisms. A concentrated release of peroxide can overpower a microbe's normal ability to use catalyase—an enzyme that degrades hydrogen peroxide—and protect itself from oxidizing agents. The rapid and overwhelming action of reactive oxygens oxidizes and decomposes any exposed organic structures, including lipids, lipid membranes, and membrane proteins, beyond the ability or capacity for the cell to repair itself. Hence, the microbial cell dies. Even a viral protein coat of a virus can be irrevocably damaged by rapid oxidation resulting in either the molecular inactivation or death of the virus.

The present peroxide coating can produce a broad spectrum, quick kill of about 90% of bacteria in a given sample within about 15 minutes by oxidizing or dissolving all organic matter for no recoverable bacteria population. Preferably, the oxidization exhibits a 95% or better microbe kill rate within about 10 minutes, and more preferably about a 95% rate at about 5 minutes or less after contact.

The formulations can be applied to the substrate or incorporated within the substrate surface. The peroxide compound can be applied to either polymer-based elastomeric or nonwoven materials through a variety of processes, such as heated spray coating, dip and squeeze in a bath or spaying, or Gravier or Meyer rod processes can be used to add the formulation to the substrate surface with air drying. Preferably the substrate is coated with an evenly distributed, uniform layer of the anti-microbial cationic and stabilized peroxide compounds. The substrate may be made from a variety of materials, including for example, elastic polymers, olefins, natural and synthetic fiber-based sheets and laminates, and may take the form of a membrane, or geometric solid.

To ensure that the peroxide compounds are not activated prematurely, a number of treated protective or cleaning articles can be stored in an air-tight, dry container, such as bags or jars, preferred, with a desiccating packet to maintain low moisture content with the container.

It is envisioned that the peroxide containing coating can be applied to a number of articles that can be found in hospital/health care, food preparation, industrial, institutional, or home settings. These articles, may include gloves, cover gowns, or cleaning substrates or wipers.

Currently, gloves have been developed to limit the transfer of microbes from the glove to environmental surfaces. This technology employs a coating of quaternary ammonium compounds (QAC) on the external surfaces of the glove substrate, which serves as an attractant of microbes through an electrostatic charged mechanism. This mode of action uses the net negative charge associated with the surfaces of biological or microbial cells, which are attracted to the cationic charge of QAC on the substrate. This technique has been effective to increase the removal of microbes from skin when using wipes and other articles that have been impregnated with cationic compounds.

Figure 3:
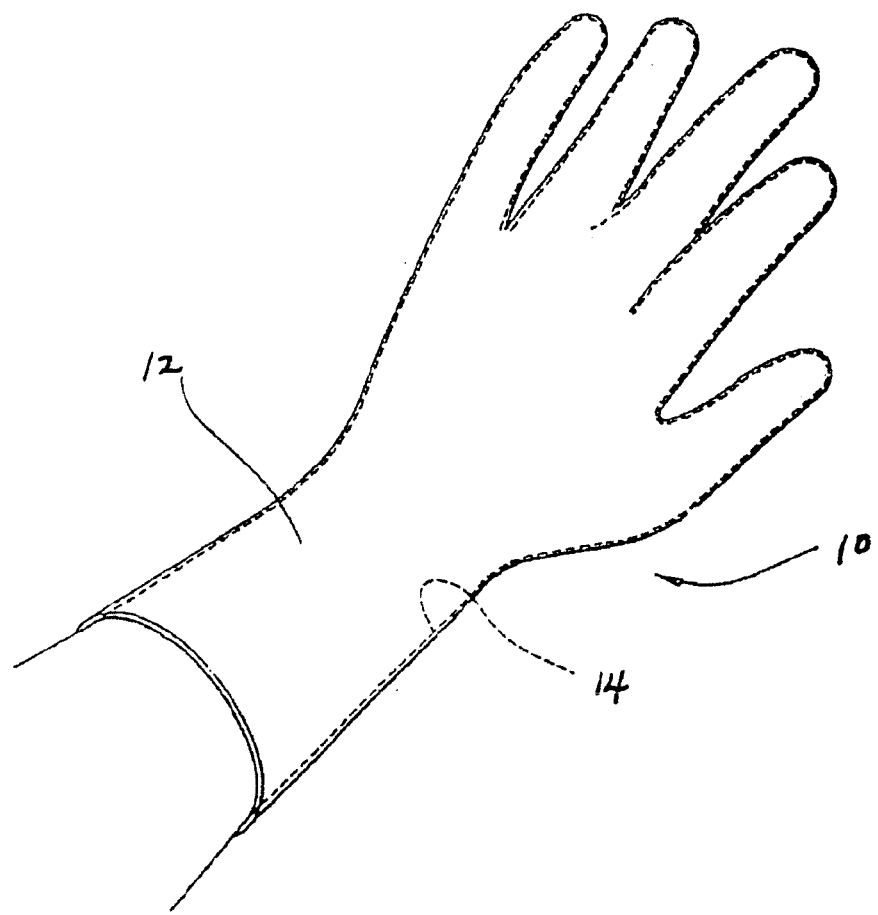
FIG. 3 shows a glove that has been prepared with an anti-microbial treatment according to an embodiment of the present invention.

In the healthcare and hospital environment, contamination or improper handling of many materials, instruments, and other articles that may contact patients can be a route of infection transfer. The ability to impart a rapid acting anti-microbial agent or coating to natural and synthetic polymer latex gloves would be a significant improvement in controlling cross-contamination between clinician and patient. According to embodiments, such as examination or work gloves or other garment articles that are worn against or in close proximity to human skin, the peroxide enabled surface is typically applied to the final outer surface, directed away from the wear's skin. FIG. 3, is a general representation of a glove 10 with a surface 12 that can be treated with stabilized peroxide compounds 14, which when activated can generate an oxidizing micro-atmosphere near or around the surface of the glove to kill microbes that are near of in contact with the surface.

In embodiments that use a carbohydrate-hydrogen peroxide or a hydrogel-hydrogen peroxide mixtures for reducing the amount of microbes, the process for preparing a product involves mixing a carbohydrate or a hydrogel and hydrogen peroxide and then freeze drying the mixtures to remove any solvent in the mixture and produce solid particles. (See for example, detailed description in "A Guide to Freeze Drying for the Laboratory," LABCONCO, Kansas City, Mo., 2004, (www.labconco.com).) Because certain peroxides are typically sensitive to heat, which may deactivate the compound, a freeze-drying process is desirable. The temperature of the mixture in solution is lowered (generally about −25.degree. C. or −30.degree. C.) to well below the freezing temperature of water and the water is sublimated off.

Alternatively, some other peroxide compounds can be prepared according to a hot or heated approach to drive off water in making the peroxide compound, such as an alcohol hydrogen peroxide mix (e.g., mannitol peroxide combination). This process can stabilize the sugar and alcohol mixture. The mixture is heated to a temperature of at least about 90.degree. C. for at least about 4.5 hours to evaporate water. Desirably, the mixture is heated to a temperature of about 97.degree. C. for about 7 hours. Finally, the solid particles produced are incorporated into the product. In certain iterations, the material is heated at a higher temperature at about 100-110.degree. C. for up to 4.5 hours. (See further, S. Tanatar, "Double Compounds of Hydrogen Peroxide with Organic Substances," JOURNAL OF THE RUSSIAN PHYSICAL CHEMICAL SOCIETY, 1909,40:376.).

The freeze-drying process, however, is likely to provide a higher yield end product then a heating method depending on the kind of peroxide product desired.

For urea-peroxide compositions, there is no need for heating step. A dry sample of the peroxide compound should have less than about 2-5% hydration content by weight. The dry peroxide compound can be milled into a powder with a mean particle size of about 5 nm or smaller. Agglomerations of the peroxide particles can be are about 15-20 nm or smaller.

A process for treating a substrate with an oxidizing compound, the process may involve providing a peroxide-containing compound and applying it either onto a surface of the substrate of the substrate or incorporating it into the substrate such that the peroxide-containing compound is generated in-situ on or in the substrate, provided that sufficient moisture is able to permeate into the substrate to interact and activate with the peroxide compound. The in-situ formation of peroxide can be accomplished by means of either a freeze-dry method or a heated method, such as described above. The predetermined choice of method can depend on the type or nature of the peroxide-containing compound and/or the physical properties or characteristics of the substrate.

During the application of peroxide it is desirable to minimize exposing the treated substrate to heat so that the peroxide moieties are not prematurely deactivated or reacted with the immediate environment. One can apply a first layer or coating that includes a carrier or host for the peroxide. This coating may also contain another class or type of anti-microbial agent. Following drying of the first layer a peroxide formulation is applied onto the first layer to associate with the carriers with minimal drying. This application can be done by means of a variety of techniques, including spray coating or roller applicators. In another embodiment, the second peroxide layer can be an anhydrous, powder such as $CaO_2$ or a non-aqueous organic peroxide, without need for drying. In another example, after applying the first layer, one can also use a printing process, such as, valve-jet, digital, or piezo-electro devices, to apply micro-droplets of peroxide solution in localized areas or patterns in similar fashion as inks for creating in printed graphics.

The peroxide compounds can be associated directly with or on the treated substrate surface. Alternatively, it is envisioned in certain embodiments that a product according to the invention may have as part of the exterior or active surface of a substrate degradable hollow structures, such as fibers, filaments, beads or other forms, in which one can fill and store peroxide agents. A source of significant moisture or the presence of specific biological or microbial secretions may serve as a trigger to breakdown the hollow structure. Once the substrate contacts such triggers, the encapsulating hollow structures may begin to dissolve and release the peroxide within, in either a prolonged, measured fashion or fast, explosive fashion onto the substrate surface to kill against nearby microbes.

Section B

A variety of different kinds of substrates can be treated or coated with the present anti-microbial composition. According to certain embodiments, the substrate materials may include, for example, elastomeric membranes, films or foams, such as natural rubber or synthetic polymer latex, soft and hard rubber or plastics, or metal, glass or ceramic surfaces, such as found with medical devices and/or surgical equipment and instruments, or hospital physical plant. Alternatively, other embodiments may have substrate materials that are selected from either woven or non-woven fabrics. Woven fabrics may be made from natural fibers (e.g., cellulose, cotton, flax linen) or a blend of natural and synthetic fibers (e.g., thermoplastics, polyolefin, polyester, nylon, aramide, polyacrylic materials). A wide variety of elastic or non-elastic thermoplastic polymers may be used to construct non-woven substrate materials. For example, without limitation, polyamides, polyesters, polypropylene, polyethylene, copolymers of ethylene and propylene, polylactic acid and polyglycolic acid polymers and copolymers thereof, polybutylene, styrenic co-block polymers, metallocene-catalyzed polyolefins, preferably with a density of less than 0.9 gram/$cm^3$, and other kinds of polyolefins, for the production of various types of elastic or non-elastic fibers, filaments, films or sheets, or combinations and laminates thereof.

A nonwoven web or laminate can be treated with compositions and methods of the present invention to impart broad spectrum anti-microbial and antistatic properties at desired or predetermined locations on the substrate, while maintaining desired physical or mechanical properties. Furthermore, the components of the treatment composition can be applied in separate steps or in one combined step. It should also be understood that the method and anti-microbial surface treatment of nonwoven materials with topical application of ingredients of this invention may incorporate not only multiple ingredients for improved anti-microbial performance but may also be used to incorporate other ingredients, such as anti-static agents which may afford dissipation of static charge build up, and skin care agents such as emollients.

Embodiments of the present anti-microbial composition may include a protective article, such as gloves, face masks, surgical or medical gowns, drapes, shoe covers, or fenestration covers. For purpose of illustration, the beneficial properties of the present invention can be embodied in a facemask containing a combination of one or more anti-microbial agents and co-active agents that rapidly inhibit and control the growth of a broad spectrum of microorganisms on the surface of the product both in the presence and absence of soil loading. The anti-microbial coating, which rapidly kills or inhibits, can be selectively placed on the exterior nonwoven facing of the mask rather than throughout the entire product. The anti-microbial agents are non-leaching from the surface of the mask in the presence of fluids, and/or are not recoverable on particles that may be shed by the mask in use and potentially inhaled by the user as measured using a blow-through test protocol. Exemplary face masks and features incorporated into face masks are described and shown, for example, in the following U.S. Pat. Nos. 4,802,473; 4,969,457; 5,322,061; 5,383,450; 5,553,608; 5,020,533; and 5,813,398. The entire contents of these patents are incorporated by reference herein in their entirety for all purposes.

The anti-microbial compositions can be applied topically to the external surfaces of nonwoven web filaments or fibers after they are formed. Desirably, a uniform coating is applied over the substrate surfaces. A uniform coating refers to a layer of anti-microbial agents that does not aggregate only at selected sites on a substrate surface, but has a relatively homogeneous or even distribution over the treated substrate surface.

Nonwoven fabrics that are treated with an anti-microbial coating of the present invention can be fabricated according to a number of processes. In an illustrative example, a method for preparing an anti-microbial treated substrate involves providing a polymer substrate and applying to the substrate the stabilized peroxide molecules. According to an embodiment, the anti-microbial composition can be applied to the material substrate via conventional saturation processes such as a so-called "dip and squeeze" or "padding" technique. The "dip and squeeze" or "padding" process can coat both sides of and/or through the bulk of the substrate with the anti-microbial composition.

As described above, various different nonwoven materials may be treated in accordance with the present disclosure. The nonwoven material may comprise, for instance, a base sheet containing cellulosic fibers alone or in conjunction with synthetic fibers. When made essentially from cellulosic fibers, for instance, the base sheet may comprise a facial tissue, a bath tissue, a paper towel, and the like. When combined with synthetic fibers, the base sheet may comprise, for instance, an airlaid web, a hydroentangled web, or a coform web. These materials are also used to produce various wiping products, including wet wipes.

Tissue products made according to the present disclosure may include single-ply tissue products or multiple-ply tissue products. For instance, in one embodiment, the product may include two plies or three plies.

In general, any suitable tissue web may be treated in accordance with the present disclosure. For example, in one embodiment, the base sheet can be a tissue product, such as a bath tissue, a facial tissue, a paper towel, an industrial wiper, and the like. Tissue products typically have a bulk of at least 3 cc/g. The tissue products can contain one or more plies and can be made from any suitable types of fiber.

Fibers suitable for making tissue webs comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Fybrel®, available from Minifibers, Inc. (Jackson City, Tenn.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a base sheet can also be utilized in the present disclosure. For example, wet laid webs can be made according to the present disclosure and can utilize creping, wet creping, double creping, embossing, wet pressing, air pressing, through-air drying, creped through-air drying, uncreped through-air drying, hydroentangling, air laying, coform methods, as well as other steps known in the art.

Also suitable for products of the present disclosure are tissue sheets that are pattern densified or imprinted, such as the tissue sheets disclosed in any of the following U.S. Pat. No. 4,514,345 issued on Apr. 30, 1985, to Johnson et al.; U.S. Pat. No. 4,528,239 issued on Jul. 9, 1985, to Trokhan; U.S. Pat. No. 5,098,522 issued on Mar. 24, 1992; U.S. Pat. No. 5,260,171 issued on Nov. 9, 1993, to Smurkoski et al.; U.S. Pat. No. 5,275,700 issued on Jan. 4, 1994, to Trokhan; U.S. Pat. No. 5,328,565 issued on Jul. 12, 1994, to Rasch et al.; U.S. Pat. No. 5,334,289 issued on Aug. 2, 1994, to Trokhan et al.; U.S. Pat. No. 5,431,786 issued on Jul. 11, 1995, to Rasch et al.; U.S. Pat. No. 5,496,624 issued on Mar. 5, 1996, to Steltjes, Jr. et al.; U.S. Pat. No. 5,500,277 issued on Mar. 19, 1996, to Trokhan et al.; U.S. Pat. No. 5,514,523 issued on May 7, 1996, to Trokhan et al.; U.S. Pat. No. 5,554,467 issued on Sep. 10, 1996, to Trokhan et al.; U.S. Pat. No. 5,566,724 issued on Oct. 22, 1996, to Trokhan et al.; U.S. Pat. No. 5,624,790 issued on Apr. 29, 1997, to Trokhan et al.; and, U.S. Pat. No. 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

If desired, various chemicals and ingredients may be incorporated into tissue webs that are processed according to the present disclosure. The following materials are included as examples of additional chemicals that may be applied to the web. The chemicals are included as examples and are not intended to limit the scope of the invention. Such chemicals may be added at any point in the papermaking process.

In general, the products of the present invention can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, emollients, and the like.

The different chemicals and ingredients that may be incorporated into the base sheet may depend upon the end use of the product. For instance, various wet strength agents may be incorporated into the product. For bath tissue products, for example, temporary wet strength agents may be used. As used herein, wet strength agents are materials used to immobilize the bonds between fibers in the wet state. Typically, the means by which fibers are held together in paper and tissue products involve hydrogen bonds and sometimes combinations of hydrogen bonds and covalent and/or ionic bonds. In some applications, it may be useful to provide a material that will allow bonding to the fibers in such a way as to immobilize the fiber-to-fiber bond points and make them resistant to disruption in the wet state. The wet state typically means when the product is largely saturated with water or other aqueous solutions.

Any material that when added to a paper or tissue web results in providing the sheet with a mean wet geometric tensile strength:dry geometric tensile strength ratio in excess of 0.1 may be termed a wet strength agent.

Temporary wet strength agents, which are typically incorporated into bath tissues, are defined as those resins which, when incorporated into paper or tissue products, will provide a product which retains less than 50% of its original wet strength after exposure to water for a period of at least 5 minutes. Temporary wet strength agents are well known in the art. Examples of temporary wet strength agents include polymeric aldehyde-functional compounds such as glyoxylated polyacrylamide, such as a cationic glyoxylated polyacrylamide.

Such compounds include PAREZ 631 NC wet strength resin available from Lanxess of Trenton, N.J., and HERCO-BOND 1366, manufactured by Hercules, Inc. of Wilmington, Del. Another example of a glyoxylated polyacrylamide is PAREZ 745, which is a glyoxylated poly (acrylamide-co-diallyl dimethyl ammonium chloride).

For facial tissues and other tissue products, on the other hand, permanent wet strength agents may be incorporated into the base sheet. Permanent wet strength agents are also well known in the art and provide a product that will retain more than 50% of its original wet strength after exposure to water for a period of at least 5 minutes.

Once formed, the products may be packaged in different ways. For instance, in one embodiment, the sheet-like product may be cut into individual sheets and stacked prior to being placed into a package. Alternatively, the sheet-like product may be spirally wound. When spirally wound together, each individual sheet may be separated from an adjacent sheet by a line of weakness, such as a perforation line. Bath tissues and paper towels, for instance, are typically supplied to a consumer in a spirally wound configuration.

The basis weight of base sheets made in accordance with the present disclosure can vary depending upon the final product. For example, the process may be used to produce bath tissues, facial tissues, paper towels, industrial wipers, and the like. In general, the basis weight of the tissue products may vary from about 10 gsm to about 110 gsm, such as from about 20 gsm to about 90 gsm. For bath tissue and facial tissues, for instance, the basis weight may range from about 10 gsm to about 40 gsm. For paper towels, on the other hand, the basis weight may range from about 25 gsm to about 80 gsm.

The tissue web bulk may also vary from about 3 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will generally be the same as indicated above, such as from about 20 gsm to about 110 gsm. Thus, the basis weight of each ply can be from about 10 gsm to about 60 gsm, such as from about 20 gsm to about 40 gsm.

In one embodiment, tissue webs made according to the present disclosure can be incorporated into multiple-ply products. For instance, in one embodiment, a tissue web made according to the present disclosure can be attached to one or more other tissue webs for forming a wiping product having desired characteristics. The other webs laminated to the tissue web of the present disclosure can be, for instance, a wet-creped web, a calendered web, an embossed web, a through-air dried web, a creped through-air dried web, an uncreped through-air dried web, a hydroentangled web, a coform web, an airlaid web, and the like.

In addition to wet lay processes, it should be understood that various other base sheets may be treated in accordance with the present disclosure. For instance, other base sheets that may be treated in accordance with the present disclosure include airlaid webs, coform webs, and hydroentangled webs.

Airlaid webs are formed in an air forming process in which a fibrous nonwoven layer is created. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

Another material containing cellulosic fibers includes coform webs. In the coform process, at least one meltblown diehead is arranged near a chute through which other materials are added to a meltblown web while it is forming. Such other materials may be natural fibers, superabsorbent particles, natural polymer fibers (for example, rayon) and/or synthetic polymer fibers (for example, polypropylene or polyester), for example, where the fibers may be of staple length.

Coform processes are shown in commonly assigned U.S. Pat. No. 4,818,464 to Lau and U.S. Pat. No. 4,100,324 to Anderson et al., which are incorporated herein by reference. Webs produced by the coform process are generally referred to as coform materials. More particularly, one process for producing coform nonwoven webs involves extruding a molten polymeric material through a die head into fine streams and attenuating the streams by converging flows of high velocity, heated gas (usually air) supplied from nozzles to break the polymer streams into discontinuous microfibers of small diameter. The die head, for instance, can include at least one straight row of extrusion apertures. In general, the microfibers may have an average fiber diameter of up to about 10 microns. The average diameter of the microfibers can be generally greater than about 1 micron, such as from about 2 microns to about 5 microns. While the microfibers are predominantly discontinuous, they generally have a length exceeding that normally associated with staple fibers.

In order to combine the molten polymer fibers with another material, such as pulp fibers, a primary gas stream is merged with a secondary gas stream containing the individualized wood pulp fibers. Thus, the pulp fibers become integrated with the polymer fibers in a single step. The wood pulp fibers can have a length of from about 0.5 millimeters to about 10 millimeters. The integrated air stream is then directed onto a forming surface to air form the nonwoven fabric. The nonwoven fabric, if desired, may be passed into the nip of a pair of vacuum rolls in order to further integrate the two different materials.

Natural fibers that may be combined with the meltblown fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

When containing cellulosic materials such as pulp fibers, a coform material may contain the cellulosic material in an amount from about 10% by weight to about 80% by weight, such as from about 30% by weight to about 70% by weight. For example, in one embodiment, a coform material may be produced containing pulp fibers in an amount from about 40% by weight to about 60% by weight.

Hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 50% to about 80% by weight, such as in an amount of about 70% by weight. Commercially available hydroentangled composite webs as described above are commercially available from the Kimberly-Clark Corporation under the name HYDROKNIT. Hydraulic entangling is described in, for example, U.S. Pat. No. 5,389,202 to Everhart, which is incorporated herein by reference.

When treating substrates containing cellulosic fibers, in general, any of the above described peroxide-containing compounds can be used. In one particular embodiment, for instance, the anti-microbial composition applied to the base sheet may comprise hydrogen peroxide complexed with a polymer, such as polyvinylpyrrolidone. The resulting hydrogen peroxide complex is stable and when contacted with water, spontaneously decomposes and releases active hydrogen peroxide.

When applied to a base sheet, various other additives and ingredients can be combined into the anti-microbial composition. For instance, in one embodiment, one or more thickening agents and/or emulsifiers may be added to the composition. One example of a thickening agent, for instance, may comprise polyethylene glycol. A suitable emulsifier, on the other hand, comprises an ethoxylated fatty alcohol. It should be understood, however, than any suitable thickening agent and/or emulsifier may be used.

When the anti-microbial composition is applied to a base sheet, in many applications, the composition should be applied without combining the composition with any significant amounts of water. For example, in one embodiment, the composition applied to the base sheet can be substantially water-free such that the peroxide complex is in a dehydrated state.

As described above, any suitable method may be used to apply the anti-microbial composition to a base sheet. In one particular embodiment, for instance, the anti-microbial composition may be extruded onto the base sheet similar to the process disclosed in U.S. Pat. No. 6,805,965, which is incorporated herein by reference. For instance, the anti-microbial composition can be extruded through a die and formed into fibers as the composition is applied to the base sheet or other article. In general, any suitable extrusion device can be used to apply the composition to the web. In one particular embodiment, for instance, the composition is extruded through a meltblown die, such as a uniform fiber depositor, forming fibers that are attenuated prior to being applied to the base sheet.

The meltblown die, for example, can have a plurality of nozzles at a die tip. The nozzles can be arranged in one or more rows along the die tip. The fibers exiting the nozzles can have a diameter of from generally about 5 microns to about 100 microns or greater.

As described above, the anti-microbial composition of the present disclosure may be combined with various different additives. In one embodiment, especially when treating base sheets containing cellulose fibers, the anti-microbial composition can be combined with one or more softening agents and applied to a base sheet. In the past, for instance, various multi-ply facial tissues have been produced in which one of the plys was treated with a softening agent, while a different ply was treated with an anti-viral composition, such as citric acid. According to the present disclosure, however, both chemistries can be combined together and applied to a tissue web in a single operation.

The softening agent can be incorporated into the anti-microbial composition in various different ways. For instance, in one embodiment, the softening agent can be part of the peroxide complex. In an alternative embodiment, a softening agent can be blended with the peroxide complex to form a single composition that is applied to the base sheet.

Various different techniques and methods may be used in order to incorporate a softening agent directly into a peroxide complex. For instance, in one embodiment, a peroxide can be complexed with a polymer. A softening agent, in turn, can be bonded to the polymer for incorporation into the complex. For example, in one embodiment, the anti-microbial composition can comprise a complex of a peroxide and a copolymer of a vinylpyrrolidone and another monomer or monomers that provide the properties of a softening agent. The monomer or monomers can be, for instance, acrylics, vinyl esters, vinyl ethers, anhydrides, olefins, and mixtures thereof.

In the above example, the vinylpyrrolidone copolymer, in the chemical composition, serves as a hydrogen peroxide stabilizing agent as well as a tissue softening agent. The distribution of vinylpyrrolidone in the copolymer can be random or can be as blocks. Having the vinylpyrrolidone copolymer as a block copolymer may provide various advantages and benefits in certain situations. For instance, the block copolymer may be more effective in some applications for stabilizing hydrogen peroxide.

When vinylpyrrolidone is applied to a base sheet as a homopolyer, the polymer may increase the stiffness of the sheet. Applying a vinylpyrrolidone copolymer as described above, on the other hand, may actually serve to increase the softness and lower the stiffness of the sheet. In particular, the vinylpyrrolidone copolymer can impart soft handfeel to the base sheet.

Suitable vinylpyrrolidone copolymers that may be used according to the present disclosure generally include copolymers that do not form stiff films. Thus, in one embodiment, the copolymer is not a film forming polymer or only forms soft films.

Suitable examples of vinylpyrrolidone copolymers are as follows:

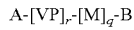

Wherein A and B are independently a hydrogen, a pyrrolidone, or a C1 to C10 Alkyl radical; VP represents a chemical unit derived from a vinylpyrrolidone and M is a chemical unit derived from a monomer such as vinyl acrylic acid, vinyl acrylic ester, vinyl acrylic amide, vinyl methacrylic amide, vinyl ester, vinyl ether or an olefin or a mixture of theses monomers. A preferred monomer for these copolymers carries a fatty group or a polysiloxane group.

Examples of suitable monomers of the suitable PVP copolymers are: dodecyl acrylate, N-[12-(dimethylamino) dodecyl]methacrylamide, octadecyl methaacrylamide, vinyl octylate, dodecyl vinyl ether, nonene, or maleic anhydride and its derivatives.

In the above formula, r and q can be as follows:
r=100 to 100,000; q=10 to 10,000

In an alternative embodiment, instead of incorporating the softening agent directly into the peroxide complex, a softening agent can be blended with the anti-microbial agent. In general, any suitable softening agent that does not adversely interact with the peroxide complex may be used. Suitable softening agents include, for instance, polysiloxanes, fatty alkyl derivatives, and/or other organic molecules like glycerine and sorbitol.

Polysiloxanes suitable for purposes of this disclosure can have one or more pendant functional groups such as amine, quaternium, aldehyde, epoxy, hydroxy, alkoxyl, polyether and carboxylic acid and its derivatives, such as amides and esters. Particularly suitable polysiloxanes have the following general structure:

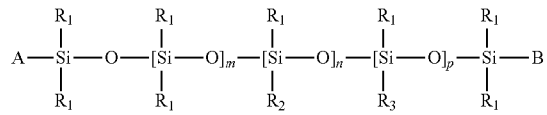

wherein:
"m" is from 10 to 100,000;
"n" is from 1 to 10,000;
"p" is from 0 to 1,000;
"A" and "B" are independently a hydroxyl, $C_1$ to $C_{20}$ or $R_2$;
$R_1$, $R_2$ and $R_3$ are distributed in random or block fashion;
$R_1$ is a $C_1$ to $C_8$ radical, which can be straight chain, branched or cyclic;
$R_2$ is a $C_1$ to $C_8$ radical, which can be straight chain, branched or cyclic, or of the structure:

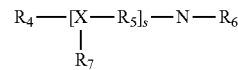

wherein
$R_4$ and $R_5$ are independently a $C_2$ to $C_8$ alkylene diradical, which can be straight chain or branched, substituted, or unsubstituted;
X is an oxygen or N—$R_8$;
$R_6$, $R_7$ and $R_8$ are independently hydrogen, a substituted or unsubstituted $C_1$ or $C_2$, a substituted or unsubstituted straight chain or branched or cyclic $C_3$ to $C_{20}$ alky radical, or an acyl radical, such as an acetyl radical; and
"s" is 0 or 1;
$R_3$ is of the structure: $R_9$—Y—$[C_2H_4O]_r[C_3H_6O]_q$—$R_{10}$
wherein
Y is an oxygen or N—$R_{11}$;
$R_9$ is a $C_2$ to $C_8$ alkylene diradical, which can be straight chain or branched, substituted or unsubstituted;
$R_{10}$ and $R_{11}$ are independently hydrogen, a substituted or unsubstituted $C_1$ or $C_2$, a substituted or unsubstituted, straight chain or branched or cyclic $C_3$ to $C_{20}$ alkyl radical;

"r" is from 1 to 100,000; and

"q" is from 0 to 100,000.

When $R_2=R_1$, "A" and "B" can also be a nitrogen quarternium.

Examples of suitable commercially available polysiloxanes include AF-2340, AF-2130, AF-23, HAF-1130, EAF-3000, EAF-340, EAF-15, AF-2740, WR-1100, WR-1300 and Wetsoft CTW from Kelmar/Wacker; DC-8822, DC-8566, DC-8211, DC-SF8417, DC-2-8630, DC-NSF, DC-8413, DC-SSF, DC-8166 from Dow Corning; SF-69, SF-99 SF-1023 from GE Silicones and Tegopren 6924, Tegopren 7990, Tego IS4111 from Goldschmidt/Degussa.

The amount of the polysiloxane in the softening composition, on a solids basis, can be from about 30 to about 75 weight percent, more specifically from 30 to about 70 weight percent, more specifically from about 40 to about 70 weight percent, and still more specifically from about 50 to about 70 weight percent.

Fatty alkyl derivatives particularly suitable for purposes of this invention can have the following general structure:

$$R_{14}\text{-}G$$

wherein:

$R_{14}$ is a $C_8$ to $C_{40}$ alkyl radical, which can be substituted or unsubstituted, primary, secondary or tertiary; straight chain, branched or cyclic; and "G" is hydroxy, amine, sulfonate, sulfate, phosphate, acid or acid derivative, or -Q-$[C_2H_4O]_i$—$[C_3H_6O]_j$—$[C_tH_{2t}O]_v$—$R_{13}$ radical;

wherein

"Q" is an oxygen radical, an NH radical or N—$[C_2H_4O]_i$—$[C_3H_6O]_j$—$[C_tH_{2t}O]_v$—$R_{13}$ radical;

$R_{13}$ is a hydrogen, a substituted or unsubstituted $C_1$ to $C_6$ alkyl radical, a straight chain or branched $C_1$ to $C_6$ alkyl radical, or a cyclic $C_1$ to $C_6$ alkyl radical;

"i", "j" and "v" are independently from 0 to 100,000, where the oxide moieties are distributed along the polymer backbone randomly or as blocks;

"i+j+v" is equal to or greater than 10; and

"t" is from 4 to 10.

Examples of commercially available suitable fatty alkyl derivatives are 9-EO ethoxylated tridecylalcohol, Ceteth-10, Ceteth-12 (12-EO ethoxylated cetyl alcohol) and Ceteth-20. More particularly, suitable commercially available fatty alkyl derivatives include Pluraface A-38, Macol CSA 20 and Macol LA 12 from BASF; Armeen 16D, Armeen 18D, Armeen HTD, Armeen 2C, Armeen M2HT, Armeen 380, Ethomeen 18/15 Armid 0, Witconate 90, Witconate AOK, and Witcolate C from Akzo Nobel and Tergitol 15-S-9, Tergitol 15-S-7, Tergitol 15-S-12, Tergitol TMN-6, Tergitol TMN-10, Tergitol XH, Tergitol XDLW, and users.

The amount of the fatty alkyl derivative in the composition, on a solids basis, can be from 0 to 60 weight percent, more specifically from about 1 to about 60 weight percent, more specifically from about 1 to about 50 weight percent, more specifically from about 10 to about 50 weight percent, more specifically from about 20 to about 50 weight percent, and still more specifically from about 20 to about 40 weight percent.

The amount of other organic chemicals such as glycerin, can be from 0 to 80 weight percent.

The weight ratio of anti-microbial agent, polyvinylpyrrolidone hydrogen peroxide, to the softening agent can be from about 0.05 to about 5; the preferred ratio can be from about 0.1 to about 2. A polyvinylpyrrolidone hydrogen peroxide can contain up to 20 weight percent of hydrogen oxide.

As described above, nonwoven webs containing cellulosic fibers made in accordance with the present disclosure can be used to form various products. Such products include bath tissues, facial tissues, paper towels, industrial wipers, and the like. In one embodiment, the anti-microbial composition containing a peroxide complex can be incorporated into a wet wiper. In this embodiment, the wet wiper may comprise any suitable base sheet such as those described above. For instance, the base sheet may comprise a wet laid web, an air formed web, a hydroentangled web, a coform web, or the like. In addition to being treated with the anti-microbial composition, the base sheet may also contain a wiping solution. The wiping solution, for instance, can be substantially water-free and can contain any ingredients that do not interfere with the peroxide complex.

In various embodiments, for instance, the wiping solution may comprise, for instance, one or more alcohols, such as an aliphatic alcohol having from about 1 to about 6 carbon atoms. The alcohol may be, for instance, methanol, ethanol, propanol, isopropanol, and the like.

Other components that may be contained in the wiping solution include disinfectants, antiseptics, emollients, skin conditioners, sanitizers, and the like. Other chemicals that may be incorporated into the wiping solution include glycols and glycerides. In addition, the wiping solution may contain one or more surfactants. In general, any suitable nonionic, anionic, cationic, or amphoteric surfactant may be used, as long as the surfactant does not negatively interfere with the peroxide complex.

The present inventive products comprise a substrate carrying a cationic compound that is highly effective in binding numerous contaminants including fungi, yeasts, molds, protozoan, viruses, soils, and other substances. Microbes are immobilized through electrostatic interactions against the cationic charged substrate. The cationic compounds impregnated into or onto the products of the present invention do not necessarily kill or inhibit the growth of microbes, but displace and bind the predominantly negatively charged microbes or other contaminants from the wound surface through positive-negative or negative-positive electrostatic interactions. This is highly advantageous in that the products of the present invention do not require an anti-microbial, bactericidal or bacteriostatic ingredient to be highly effective in safely cleaning skin. When the products of the present invention are utilized in or around skin wounds, microbes are not simply killed and left in the wound, but are actually bound to the cationic compounds in or on the fibers of the product and removed from the skin. This may significantly reduce the chance of further infection in and around the wound. Further, the cationic compounds used in the products of the present invention are substantially non-toxic and non-irritating to the wound and surrounding skin.

Without being bound to a particular theory, it appears that by increasing the attractive forces between the product containing the cationic compounds and the microbe and/or contaminant on or near the skin or wound surface in excess of the forces attracting the microbe and/or contaminant to the skin, cleaning of the skin can be significantly enhanced by dislodging and binding the contaminant to the cationic species added to the product. It appears that the cationic compounds interact with the overall net negative charge of the microbe and/or contaminant causing the detachment of the microbe and/or contaminant from the skin through an electrostatic interaction. The interaction between the cationic compounds and the microbe and/or contaminant appears to be stronger than the combined forces of adhesion that retain the microbe and/or contaminant on or near the skin including hydrophobic interactions, electrostatic interactions, and ligand interactions. Because the microbe and/or contaminant is released from the skin and bound to the charge modified product, it may be easily and efficiently carried away by the product. This is highly advantageous over more traditional products as the contaminant is not merely dislodged from the skin or wound surface, but is dislodged and then removed from the surface through interactions with the substrate containing the cationic compounds. A suitable amount of cationic compounds are added to the products of the present invention such that the forces binding the contaminant to the skin surface, such as hydrophobic interactions, electrostatic interactions, and ligand interactions, can be overcome by the attraction to the cationic species.

In accordance with the present invention, numerous microbes and soils such as, for example, *Candida albicans*, can be effectively captured and removed away from mammalian skin or a substrate surface by means of a cleansing product or substrate having a sufficient amount of cationic compounds, such as, for example, octadecyl-dimethyl-trimethoxyl-silpropyl-ammonium chloride, having a suitable effective charge density or anion exchange capacity which modifies the overall charge density of the product. It has been discovered that by providing a substrate comprising a sufficient amount of cationic compounds having an effective charge density of from about 0.1 microequivalents/g to about 8000 microequivalents/g or more, the substrate surface can be electrically altered such that the resulting product has a Positive Charge Index as defined herein of at least about 35 positive charge units, more typically about 50 or above, and preferably about 52-250 or 300. Such a Positive Charge Index allows numerous types of microbes and contaminants to be electrostatically dislodged from the skin surface, captured and carried away. The cationic compound-containing products of the present invention are safe for use on the skin and in and around wounds, as microbes are removed from the wound surface without a substantial risk of rupturing, and thus the risk of introduction of byproducts from the microbe into wounds is minimized or eliminated. In some desired embodiments, the substrate carries a cationic compound capable of binding contaminants located on the skin. Preferably, the cationic compound has an effective charge density of from about 500 or 1000 microequivalents/g to about 8000 microequivalents/g and the product has a Positive Charge Index of at least 52. The substrate can be made into a product comprising either a woven or a non-woven web material and a cationic compound capable of binding contaminants located on the surface of skin.

The cationic compounds described herein can be incorporated into or onto a substrate or product utilizing numerous methods. In one embodiment of the present invention, the cationic compounds are impregnated into the fibers comprising the underlying substrate of the cleansing product during the substrate manufacturing process. Although generally referred to herein as "pulp fibers" or "cellulose fibers," it should be recognized that various types of fibers, including wood pulp fibers and synthetic and polymer-type fibers, are suitable for substrate use in the cleansing products of the present invention, and are within the scope of the present invention. Suitable substrates for incorporation of the cationic compounds include, for example, cellulosic materials, coform materials, woven webs, non-woven webs, spunbonded fabrics, meltblown fabrics, knit fabrics, wet laid fabrics, needle punched webs, or combinations thereof.

Examples of suitable cationic compounds that can be utilized to increase the overall effective cationic charge density of the cleansing products of the present invention include, for example, polyquaternary ammonium compounds, such as those sold under the tradename Bufloc 535 (Buckman Laboratories International, Memphis, Tenn.), Nalco 7607 (ONDEO NALCO Company, Naperville, Ill.), Reten 201 (Hercules Inc., Wilmington, Del.), Cypro 515 (CIBA Speciality Chemicals, Suffolk, Va.), Bufloc 5554 (Buckman Laboratories International, Memphis, Tenn.), and Busperse 5030 (Buckman Laboratories International, Memphis, Tenn.) and cationic polymers, inorganic cationic species, biological cationic polymers, modified chitosan, octadecyidimethyltrimethoxylsilpropylammonium chloride, octadecyidimethoxylsilpropylammonium chloride, polyacrylamides, diallydimethylammonium chloride, dicyandiamideformaldehyde, epichlorohydrinamine, cationic liposomes, modified starch, 1-methyl-2-Noroleyl-3-oleyl-amidoethyl imidazoline methylsulfate, 1-ethyl-2-Noroleyl-3-oleyl-amidoethyl imidazoline ethylsulfate, trimethylsilylmodimethicone, amodimethicone, polyquaternium-2, polyquaternium-4, polyquaternium-5, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-32, polyquaternium-33, polyquaternium-34, polyquaternium-35, polyquaternium-36, polyquaternium-37, polyquaternium-39, polysilicone-1, polysilicone-2, and mixtures and combinations thereof. Especially preferred compounds include quaternary compounds, polyelectrolytes, octadecyldimethoxylsilpropylammonium chloride, 1-methyl-2-Noroleyl-3-oleyl-amidoethyl imidazoline methylsulfate, and 1-ethyl-2-Noroleyl-3-oleyl-amidoethyl imidazoline ethylsulfate. It would be recognized by one skilled in the art that other cationic compounds commonly used in pulp manufacturing processes could also be utilized in accordance with the present invention to significantly increase the overall cationic effective charge density of the resulting product.

The cationic compounds for incorporation into products of the present invention have a net cationic charge, and may sometimes be referred to as anion exchangers. Typically, the products of the present invention contain cationic compounds having sufficient positive charge to impart improved cleaning characteristics into the products through electrostatic interactions with microbes and/or contaminants and skin. The amount of "cationic charge" on a particular compound can vary substantially and can be measured utilizing several different units. Anionic exchangers are sometimes referred to as having a "capacity" which may be measured in microequivalents per gram or milliequivalents per gram, or may be measured in terms of the amount of a certain compound or protein that the anionic exchanger will bind. Still another way of referring to the amount of positive charge is in terms of micro or milliequivalents per unit area. One skilled in the art will recognize that the exchange capacity units can be converted from one form to another to calculate proper amounts of anion exchanger for use in the present invention.

In accordance with the present invention, the chemical additives utilized to increase the overall effective cationic charge density of the resulting product have a cationic charge. Cationic compounds useful in the present invention typically have an effective charge density of from about 0.1 microequivalents/g to about 8000 microequivalents/g, more preferably from about 100 microequivalents/g to about 8000 microequivalents/g, still more preferably from about 500 microequivalents/g to about 8000 microequivalents/g, and most preferably from about 1000 microequivalents/g to about 8000 microequivalents/g. Although effective charge densities of more than about 8000 microequivalents/g can be used in the cleansing products of the present invention, such a large charge density is not typically required to realize the benefit of the present invention, and may result in the deterioration of product properties. As the effective charge density of the cationic material increases, the amount of cationic material required to be added to the pulp manufacturing process typically decreases. Generally, from about 0.01% (by weight of the substrate) to about 25% (by weight of the substrate), preferably from about 0.01% (by weight of the substrate) to about 10% (by weight of the substrate) of cationic material having the above-described effective charge density will be sufficient to increase the overall cationic charge of the resulting product sufficiently for purposes of the present invention. The actual amount of cationic material required for introduction into the pulp manufacturing process may be influenced by numerous other factors including, for example, the amount of steric hindrance in the pulp fibers due to other additives present in the pulp fiber environment, the accessibility of the charges on the pulp fibers, competitive reactions by cationic materials for anionic sites, the potential for multilayer adsorption into the pulp fiber, and the potential for precipitation of anionic materials out of solution.

Without being bound to a particular theory, it is believed that many of the cationic molecules (which may sometimes also be referred to as "softeners" or "debonders") suitable for use in accordance with the present invention have a cationic charge by virtue of a quaternary nitrogen moiety. During the manufacturing of the skin cleansing product, this cationic charge may be used to attract the cationic molecule to the fiber surface, which is typically anionic in nature. The cationic compounds suitable for use in the present invention may have hydrophobic side chains which impart hydrophobicity to the molecule, making these molecules substantially non-water soluble. As such, these cationic compounds are believed to actually exist in solution as micelles of cationic compound molecules, where the hydrophobic tails are in the interior of the micelle and the cationic charges are exposed to the water phase. When a micelle cluster is adsorbed onto the fiber, more than one molecule is present on the surface, thus creating a site on the fiber with an excess of cationic charge. Once dried, these cationic molecules are likely associated with a counter-ion (although it may be possible that some are present without counter-ions which may create a static cationic charge) to form a net neutral charge. When the treated substrate comes into contact with an aqueous media such as the urine or feces, the counter-ion is free to dissociate and thus leaves the fiber cationically charged in the region with adsorbed cationic molecules. The cationic charge on the surface of the substrate is then able to attract and retain various microbes and/or contaminants which typically have a negatively charged outer surface.

Section C

Positive Charge Index Assay for Determining the Positive Charge Index of a Substrate The amount of positive charge imparted onto a substrate, such as a base sheet or woven or non-woven web, for example, can be measured in accordance with the present invention using the Positive Charge Index Assay including an anionic dye binding assay. The Positive Charge Index Assay utilizes the dye Eosin Y, which is a biological stain for alkaline materials. Eosin B can optionally be utilized in place of Eosin Y. The Positive Charge Index Assay is carried out as follows:

Step 1: Cut the substrate to be evaluated into two squares approximately 2 centimeters by 2 centimeters. The first square will be stained with Eosin Y as described herein and optically evaluated. The second square will be subjected to the same Eosin Y staining procedure described herein with the exception that the second square will not be stained with Eosin Y; that is, the second square will undergo each and every step as the first square, except Steps 5 and 6 below.

Step 2: Introduce filter paper, such a Whatman #4 Qualitative 125 millimeter filter paper or equivalent, into a Buchner Funnel attached to a vacuum source.

Step 3: Start the vacuum, and wash the filter paper with deionized water.

Step 4: Allow the filter paper to dry.

Step 5: Place the test substrate on top of the dry filter paper and saturate the substrate with 0.75 milliliters of 0.5% (weight/volume) Eosin Y prepared in deionized water.

Step 6: Allow the test substrate to soak in the Eosin Y for 2 minutes and then cover the test substrate with a dry piece of filter paper.

Step 7: Wash the test substrate through the filter paper for 3 minutes with deionized water.

Step 8: Remove the test substrate with forceps and place it on a dry piece of filter paper and allow it to dry completely.

Step 9: Measure CIELAB Color Space of the dried test substrate using a Minolta CM-508d Spectrophotometer, or similar equipment. The spectrophotometer is set for CIELAB Color Space with the following parameters: Target Status CREEMM, Color Mode L*a*b*, Observer 10.degree., and the primary Illuminant D65. A standard white block supplied by the spectrophotometer manufacturer is utilized for calibration of the instrument.

Step 10: Calculate the DE*ab value of the Eosin Y stained test substrate using an un-stained test substrate for comparison. The DE*ab value is equal to the Positive Charge Index. The higher the Positive Charge Index, the higher the positive charge on the substrate. The CIE Color System Values are set forth below:

L*=Lightness=A value 0 to 100
a*=Color coordinate red-verses-green
b*=Color coordinate yellow-verses-blue
$C = Chroma = [(a^*)^2 + (b^*)^2]^{1/2}$
$h = Hue\ angle = \arctan(b^*/a^*)$
$E = Color\ difference = [(L^*)^2 + (a^*)^2 + (b^*)^2]^{1/2}$
$DL^* = L^*_{Eosin\ Stained\ Substrate} - L^*_{Unstained\ Substrate}$
$Da^* = a^*_{Eosin\ Stained\ Substrate} - a^*_{Unstained\ Substrate}$
$Db^* = b^*_{Eosin\ Stained\ Substrate} - b^*_{Unstained\ Substrate}$
$DE^*ab = [(DL^*)^2 + (Da^*)^2 + (Db^*)^2]^{1/2}$ The cationic compounds useful in the present invention to increase the overall effective cationic charge density of a finished product can easily be incorporated into various products. As used herein, the term "cationic compound" means any compound or ingredient which increases the overall cationic charge of the fibers comprising a cleansing product when the fibers are wetted. Preferably, the cationic compounds used in accordance with the present invention to increase the overall effective charge density of a finished product are non-antagonistic to pulp fibers or to other additives utilized in the manufacturing process. Further, it is preferred that the additional cationic compounds added to the pulp in accordance with the present invention do not substantially adversely affect the overall strength and integrity of the resulting modified product.

Section D

Empirical

EXAMPLE NO. 1

Anti-microbial Coating of Material

A Biodyne B membrane (0.45 .mu.m pore size; 10 mm discs, Pall Corporation, East Hills, N.Y.) was coated with 100 .mu.l of a 50% w/v urea hydrogen peroxide in water (Sigma Chemical St. Louis, Mo.). The coated membrane was allowed to dry over night at room temperature. The total add-on was 50 mg of urea peroxide per 78.5 mm.sup.2 or 0.64 mg/mm.sup.2.

Biodyne B Membrane Description

Pore surfaces populated by a high density of quaternary ammonium groups. This results in a positive surface charge over a broad pH range. Positive charge promotes strong ionic binding of negatively charged molecules.

Microbial Challenge Experiment

About 100 .mu.l of a 6.times.10.sup.7 CFU/ml of *Klebsiella pneumoniae* ATCC 4352 suspension in phosphate buffered saline (pH 7.4) was added to the top of the Biodyne B membranes and allowed to incubate at 25.degree. C. for 15 min. The exposed Biodyne B membranes were placed in 25 ml of Letheen broth and extracted by vortexing (20 sec) and shaking on an orbital shaker (10 min). Plating was done employing a spiral plater (WASP, Microbiological Associates) on trpyticase soy agar. Counts were done utilizing a digital imaging system (ProtoCOL, Microbiological Associates). A set of 5 replicates were done. Coated Biodyne B membranes were compared to uncoated Biodyne B membranes to determine Log.sub.10 reductions.

TABLE 2

*K. pneumoniae* counts after 15 min exposure at 25° C. from Biodyne B membrane samples that are urea peroxide treated and untreated. All replicate values averages of triplicates.

| | CPU/Filter | |
|---|---|---|
| Replicate | Untreated Biodine B Membranes | Biodine B Membranes Coated with Urea Peroxide |
| 1 | $2.1 \times 10^5$ | $1.6 \times 10^3$ |
| 2 | $3.0 \times 10^3$ | 0.0E+00 |
| 3 | $5.4 \times 10^4$ | 0.0E+00 |
| 4 | $2.6 \times 10^5$ | 0.0E+00 |
| 5 | $2.4 \times 10^5$ | 0.0E+00 |
| 6 | $5.2 \times 10^5$ | 0.0E+00 |
| AVG | $2.7 \times 10^5$ | $2.6 \times 10^2$ |

No significant or detectable population in replicates 2-4, biodine B charged membrane Addition of 0.64 mg/mm.sup.2 urea peroxide to a positively charge membrane provided at .gtoreq.3 Log.sub.10 reduction of bacterial viability in 15 min at 25.degree. C. It is expected that urea peroxide can added on to a positively charged modified substrate at concentrations ranging between 1-0.01 mg/mm.sup.2 to produce adequate efficacy. Alternative peroxide types are: calcium peroxide, sodium carbonate peroxide, and carbohydrate peroxide mixtures that include dulcitol, arabitol, adonitol, mannitol, sorbitol, xylitol, lactitol, maltitol, dithioerythritol, dithiothreitol, glycerol, galactitol, erythritol, inositol, ribitol, and hydrogenated starch hydrolysates as the carbohydrate moiety. Types and add-on ranges of positively charged molecules would be expected to be in the range described in the following patent publications: U.S. 2004/0151919, U.S. 2004/0009141, U.S. 2004/0009210, and U.S. 2005/0137540, which are incorporated herein. This treatment type is applicable to woven, non-woven and/or formed polymers. Specific product forms are gloves, gowns, masks, drapes, wipes, diapers, air filters, and others.

EXAMPLE NO. 2

The following is a prophetic example.

Three-ply, wet-pressed, creped facial tissue products are made according to the present disclosure as described below.

In general, the tissue base sheets are produced using a conventional wet-pressed tissue making process well known in the art. More particularly, an aqueous suspension of papermaking fibers is issued from a layered headbox onto a forming fabric. The furnish included 70 weight percent hardwood (eucalyptus) fibers and 30 weight percent softwood fibers. A vacuum box beneath the forming fabric is adapted to remove water from the fiber furnish to assist in forming a web. The newly formed web is transferred to a felt with aid of a pick up roll. While supported by the felt, the tissue web is lightly pressed onto the surface of a Yankee dryer using a press roll. The dried web is creped from the surface of the Yankee dryer and the resulting single-ply tissue base sheet is wound onto a parent roll. Thereafter, the base sheets from three like parent rolls are unwound and converted into a three-ply base sheet for subsequent application of the various softening compositions. The finished basis weight of the three-ply base sheet is about 22.7 pounds per 2880 square feet.

In accordance with the present disclosure, an anti-microbial composition is applied to the above base sheet. The composition comprised primarily a complex of hydrogen peroxide with a linear polyvinylpyrrolidone, a polysiloxane, a polyethylene glycol, and an ethoxylated fatty alcohol. The composition is prepared to have a viscosity of about 5,000 cps and is simultaneously applied to both surfaces of the three-ply basesheet with an Uniform Fiber Depositor (a type of meltblow die). The uniform fiber depositor has 7 nozzles per inch and operates at an air pressure of 20 psi. The die applies about 5 weight percent of the composition on to the substrate.

The tissue products prepared have a soft handfeel. When a fluid containing Rhinoviruses Type 1A and 2, influenza A an B and Syncytial Virus is poured on the tissue, 99.9% of all viruses are killed in 15 minutes.

EXAMPLE NO. 3

The following example is also a prophetic example.

In this example, an anti-microbial composition in accordance with the present disclosure is applied to a paper towel, which may be made according to Example 1 as described in U.S. Pat. No. 6,727,004, which is incorporated herein by reference. The composition comprises primarily a complex of hydrogen peroxide with crosslinked polypyrrolidone, a polyethylene glycol, and an ethoxylated fatty alcohol. The composition which has a viscosity of about 15,000 cps is simultaneously applied to both surfaces of the three-ply basesheet by a Uniform Fiber Depositor at 40 degree centigrade. The uniform fiber depositor has 3 nozzles per inch and operates at an air pressure of 10 psi. The die applies about 2 weight percent of the composition on to the paper towel.

The product prepared provides a soft handfeel. When a fluid inoculated with $10^7$ counts of each of *S. aureus, E. Coli & Cloacae, P. aeruginosa & B. cepacia, C. albicans*, and *A. niger & luteus* is absorbed into the paper towel, nearly all the microorganisms are killed in 1 minute. Less than 10 counts of each of the microorganisms are detected on the tissue.

EXAMPLE NO. 4

The following is also a prophetic example.

In this example, a base sheet is prepared containing only synthetic fibers or synthetic fibers in combination with pulp fibers. The base sheet, for instance, may be as described in U.S. Pat. No. 6,887,350, which is incorporated herein by reference. The base sheet, in one embodiment, can contain 80% by weight polyester fibers and 20% by weight softwood fibers. Alternatively, the base sheet may contain 100% synthetic fibers, such as polyester fibers.

An anti-microbial composition made in accordance with the present disclosure is prepared and applied to the base sheet. The composition is an emulsion of a complex of hydrogen peroxide and a copolymer of polyvinylpyrolidone and acrylate carrying a polysiloxane moiety. The emulsion has a viscosity of about 20 cps and is simultaneously applied to both surfaces of the synthetic fiber substrate by rotogravure printing. The gravure rolls are electronically engraved, chrome over copper rolls supplied by Southern Graphics Systems, located at Louisville, Ky. The rolls have a line screen of 360 cells per lineal inch and a volume of 1.5 Billion Cubic Microns (BCM) per square inch of roll surface. Typical cell dimensions for this roll are 65 microns in length, 110 microns in width, and 13 microns in depth. The rubber backing offset applicator rolls are a 75 Shore A durometer cast polyurethane supplied by American Roller Company, located at Union Grove, Wis. The process is set up to a condition having 0.375 inch interference between the gravure rolls and the rubber backing rolls and 0.003 inch clearance between the facing rubber backing rolls. The simultaneous offset/offset gravure printer is run at a speed of 2000 feet per minute. This process yields a solids add-on level of about 1.0 weight percent based on the dry weight of the finished product.

Product treated with this composition provides a soft handfeel. When a fluid containing Rhinoviruses Type 1A and 2, influenza A and B and Syncytial Virus and *S. aureus, E. Coli & Cloacae, P. aeruginosa & B. cepacia, C. albicans*, and *A. niger & luteus* is poured into the paper tissue, more than 99.9% and all viruses and other microorganisms are killed in 1 minute.

EXAMPLE NO. 5

The following is a prophetic example.

Single-ply, three-layered uncreped throughdried bath tissue basesheets are made generally in accordance with the following procedure using eucalyptus pulp fibers for the outer layers and softwood pulp fibers for the inner layer. Prior to pulping, a quaternary ammonium oleylimidazoline softening agent (Prosoft TQ-1003 from Hercules, Inc.) is added at a dosage of 4.1 kg/Mton of active chemical per metric ton of pulp fiber to the eucalyptus furnish. After allowing 20 minutes of mixing time, the furnish is dewatered using a belt press to approximately 32% consistency. The filtrate from the dewatering process is either sewered or used as pulper make-up water for subsequent pulp fiber batches but not sent forward in the stock preparation or tissue making process.

The thickened pulp fiber containing the debonder is subsequently redispersed in water and used as the outer layer furnishes in the tissue making process. The softwood pulp fibers are pulped for 30 minutes at 4 percent consistency and diluted to about 3.2 percent consistency after pulping, while the debonded eucalyptus pulp fibers is diluted to about 2 percent consistency. The overall layered tissue sheet weight is split about 30%/about 40%/about 30% among the eucalyptus/refined softwood/eucalyptus pulp fiber layers.

A three-layered headbox is used to form the wet tissue sheet with the refined northern softwood kraft stock in the two center layers of the head box to produce a single center layer for the three-layered tissue product described. Turbulence-generating inserts recessed about 3 inches (75 millimeters) from the slice and layer dividers extending about 1 inch (25.4 millimeters) beyond the slice are employed. The net slice opening is about 0.9 inch (23 millimeters) and water flows in all four headbox layers are comparable. The consistency of the stock fed to the headbox is about 0.09 weight percent.

The resulting three-layered tissue sheet is formed on a twin wire, suction form roll, former with forming fabrics being Lindsay 2164 and Asten 867A fabrics, respectively. The speed of the forming fabrics is 11.9 meters per second. The newly-formed tissue sheet is then dewatered to a consistency of about 20 to about 27 percent using vacuum suction from below the forming fabric before being transferred to the transfer fabric, which is traveling at about 9.1 meters per second (30% rush transfer). The transfer fabric is an Appleton Wire T807-1. A vacuum shoe pulling about 6-15 inches (150-380 millimeters) of mercury vacuum is used to transfer the tissue sheet to the transfer fabric. The tissue sheet is then transferred to a throughdrying fabric (Lindsay Wire T1205-1). The throughdrying fabric is traveling at a speed of about 9.1 meters per second. The tissue sheet is carried over a Honeycomb throughdryer operating at a temperature of about 350° F. (175° C.) and dried to final dryness of about 94-98 percent consistency. The resulting uncreped tissue sheet is then wound into a parent roll.

The parent roll is then unwound and the tissue sheet is calendered twice. At the first station the tissue sheet is calendered between a steel roll and a rubber covered roll having a 4 P&J hardness. The calender loading is about 90 pounds per lineal inch (pli). At the second calendering station, the tissue sheet is calendered between a steel roll and a rubber covered roll having a 40 P&J hardness. The calender loading is about 140 pli. The thickness of the rubber covers is about 0.725 inch (1.84 centimeters).

In this example, the anti-microbial composition applied to the base sheet includes a complex of hydrogen peroxide and a copolymer of polyvinylpyrolidone and octadecyl acrylate. In addition to having anti-microbial properties, the complex also serves as a softening agent. The composition is applied as a solid powder to the base sheet via a powder coating process.

The tissue product treated with the above composition provides a soft handfeel. When a fluid containing Rhinoviruses Type 1A and 2, influenza A and B and Syncytial Virus and *S. aureus, E. Coli & Cloacae, P. aeruginosa & B. cepacia, C. albicans*, and *A. niger & luteus* is poured into the tissue, more than 99.9% and all viruses and other microoganisms are killed in 10 seconds.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

What is claimed:

1. A tissue product comprising:
a stack of individual tissue sheets or a spirally wound roll of individual tissue sheets separated by a line of weakness, each tissue sheet having a first surface and a second and opposite surface, the tissue sheets having a bulk density of at least 3 cc/g, wherein the tissue sheets contain fibers impregnated with a cationic compound;
an anti-microbial composition applied to each tissue sheet, the anti-microbial composition comprising a substantially dehydrated peroxide complex, wherein the peroxide complex comprises hydrogen peroxide complexed with a polymer and is configured to release hydrogen peroxide when the tissue sheet is contacted with water; and
a softening agent applied to each tissue sheet, wherein the weight ratio of substantially dehydrated peroxide complex to the softening agent ranges from about 0.05 to about 5, wherein the softening agent comprises a polysiloxane, a fatty alkyl derivative, or a combination thereof.

2. A tissue product as defined in claim 1, wherein the peroxide complex comprises a hydrogen peroxide-polyvinylpyrrolidone complex.

3. A tissue product as defined in claim 1, wherein the softening agent is blended with the anti-microbial composition.

4. A tissue product as defined in claim 1, wherein each tissue sheet comprises synthetic fibers.

5. A tissue product as defined in claim 1, wherein each tissue sheet comprises synthetic and pulp fibers.

6. A tissue product as defined in claim 1, wherein the anti-microbial composition is present at least on the first surface of each tissue sheet.

7. A tissue product as defined in claim 1, wherein the tissue product comprises a facial tissue, a bath tissue, or a paper towel.

8. A tissue product as defined in claim 1, wherein each tissue sheet comprises at least 70% by weight pulp fibers.

9. A tissue product as defined in claim 1, wherein the peroxide complex comprises a complex of hydrogen peroxide with a copolymer of vinylpyrrolidone with an acrylic, a vinyl ester, a vinyl ether, an anhydride, an olefin or mixtures thereof.

10. A tissue product as defined in claim 1, wherein the anti-microbial composition is present on each tissue sheet in an amount from about 0.1 percent to about 15 percent by weight.

11. A tissue product as defined in claim 1, wherein the anti-microbial composition is present on each tissue sheet in an amount such that the tissue sheet contains from about 0.5 percent to about 5 percent by weight hydrogen peroxide.

12. A tissue product as defined in claim 1, wherein the anti-microbial composition further comprises a thickening agent and an emulsifier.

13. A tissue product as defined in claim 1, wherein the anti-microbial composition further comprises polyethylene glycol.

14. A tissue product as defined in claim 1, wherein the tissue product comprises a wet wipe containing a wiping solution, the wiping solution being substantially water-free.

15. A tissue product as defined in claim 1, wherein the peroxide complex comprises hydrogen peroxide complexed with a copolymer of polyvinylpyrrolidone and an acrylate.

16. A tissue product as defined in claim 15, wherein the acrylate comprises octadecyl acrylate.

17. A tissue product as defined in claim 9, wherein the vinylpyrrolidone copolymer carries a fatty group or a polysiloxane group.

18. A tissue product as defined in claim 1, wherein the cationic compound is a quaternary ammonium compound.

19. A tissue product as defined in claim 1, wherein the cationic compound is present in an amount from about 0.01% by weight of each tissue sheet to about 25% by weight of each tissue sheet.

* * * * *

UNITED STATES PATENT AND TRADEMARK OFFICE
CERTIFICATE OF CORRECTION

PATENT NO. : 8,778,386 B2  
APPLICATION NO. : 11/847976  
DATED : July 15, 2014  
INVENTOR(S) : Kou-Chang Liu et al.

Page 1 of 1

It is certified that error appears in the above-identified patent and that said Letters Patent is hereby corrected as shown below:

On the Title Page

Item (56) Under U.S. Patent Documents add:

6,887,496    5/2005    Koenig et al.

Signed and Sealed this
Twenty-eighth Day of October, 2014

Michelle K. Lee
*Deputy Director of the United States Patent and Trademark Office*